United States Patent
Rauchschwalbe et al.

(10) Patent No.: US 6,888,005 B2
(45) Date of Patent: *May 3, 2005

(54) 2-PHENYLBENZIMIDAZOLE-5-SULPHONIC ACID FROM ISOLATED 3,4-DIAMINOBENZENESULPHONIC ACID AND USE THEREOF IN COSMETIC PREPARATIONS

(75) Inventors: Günter Rauchschwalbe, Leverkusen (DE); Herbert Emde, Köln (DE); Wolfram Kissener, Neunkirchen-Seelscheid (DE); Klaus-Christian Paetz, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/663,825

(22) Filed: Sep. 16, 2003

(65) Prior Publication Data

US 2004/0059125 A1 Mar. 25, 2004

(30) Foreign Application Priority Data

Sep. 17, 2002 (DE) ........................................ 102 43 027

(51) Int. Cl.⁷ ............................................ C07D 235/18
(52) U.S. Cl. ................... 548/310.1; 548/310.7
(58) Field of Search ........................ 548/310.1, 310.7

(56) References Cited

U.S. PATENT DOCUMENTS

| | | | |
|---|---|---|---|
| 3,624,100 A | 11/1971 | Frick et al. | 260/309.2 |
| 3,705,944 A | 12/1972 | Frick et al. | 424/273 |
| 5,473,079 A | 12/1995 | Heywang et al. | 548/305.4 |
| 5,585,091 A | 12/1996 | Pelzer et al. | 424/60 |
| 6,184,235 B1 | 2/2001 | Connor et al. | 514/322 |
| 6,348,487 B1 | 2/2002 | Connor et al. | 514/415 |
| 6,440,401 B1 * | 8/2002 | Heywang et al. | 424/59 |
| 2002/0013474 A1 | 1/2002 | Heywang et al. | 548/304.4 |
| 2003/0176438 A1 | 9/2003 | Arienti et al. | 514/252.04 |

FOREIGN PATENT DOCUMENTS

| | | |
|---|---|---|
| DE | 676 103 | 6/1939 |
| WO | 9806703 | 2/1998 |
| WO | 03032984 | 4/2003 |

OTHER PUBLICATIONS

Am. Chem. Soc. 79, 427, month unavailable (1957), D. Hein et al, "The Use of Polyphosphoric Acid in the Synthesis of 2–Aryl– and 2–Alkyl–substituted Benzimidazoles, Benzoxazoles and Benzothiazoles".

* cited by examiner

*Primary Examiner*—Rita Desai
*Assistant Examiner*—Robert Shiao
(74) *Attorney, Agent, or Firm*—Diderico van Eyl; Jennifer R. Seng; Jill Donesvich

(57) ABSTRACT

A process for the preparation of 2-phenylbenzimidazole-5-sulphonic acid, characterized in that 3,4-diaminobenzenesulphonic acid is reacted at a pH between 4 and 7 in aqueous solution with 0.9 to 1.5 mol of benzaldehyde per mole of 3,4-diaminobenzenesulphonic acid and with 1.0 to 3.0 mol of $SO_2$ per mole of 3,4-diaminobenzenesulphonic acid, or an agent which comprises 1.0 to 3.0 mol of $SO_2$ per mole of 3.4-diaminobenzenesulphonic acid, is described.

6 Claims, No Drawings

2-PHENYLBENZIMIDAZOLE-5-SULPHONIC ACID FROM ISOLATED 3,4-DIAMINOBENZENESULPHONIC ACID AND USE THEREOF IN COSMETIC PREPARATIONS

BACKGROUND OF THE INVENTION

1. Field of the Invention

2-Phenylbenzimidazole-5-sulphonic acid or its sodium salt is an important skin protectant which is added to sunscreens in order to absorb ultraviolet light at about 280–320 nm ("UV-B rays").

2. Brief Description of the Prior Art

Generally, 2-phenybenzimidazole-5-sulphonic acid or its sodium salt is known from DE-A 676 103. The product has been available commercially for a long time, for example under the name NeoHeliopan Hydro® from Haarmann&Reimer GmbH and is well known to the person skilled in the art. The relevant prior art with regard to the product is found, for example, in EP-A 669 323. For the synthesis, it has been proposed to heat 1,2-diaminobenzene, benzoic acid or derivatives of benzoic acid (such as benzoic esters or benzonitrile) and sulphuric acid together. However, the yield of pure product achieves only 49 to 60% (see DE 4 203 072).

The process can only be carried out with difficulty on an industrial scale since, under the required reaction conditions, benzoic acid sublimes out of the mixture and blocks the waste gas lines.

If 1,2-diaminobenzene is reacted with benzoic alkyl ester under acidic catalysis, then N-alkylated compounds form.

A known method consists in condensing 1,2-diaminobenzene with benzoic acid in the presence of polyphosphoric acid to give benzimidazole, and sulphonating this with, for example, chlorosulphonic acid (Am. Chem. Soc. 79, 427 (1957)).

This process cannot be realised in industry very easily since technical handling of the very viscous and expensive polyphosphoric acid is involved and not economic and in the process large amounts of phosphoric acid pass into the receiving watercourses and can eutrophicate these.

An alternative consists in condensing 1,2-diaminobenzene with benzaldehyde in the presence of sulphurous acid to give 2-phenylbenzimidazole and then further sulphonating it as described; however, it is known that under these conditions 1-benzyl-2-phenyl-benzimidazole forms as an undesired secondary product, which can only be separatred off with difficulty.

The sulphonation step is likewise problematical since among other secondary components, an isomeric sulphonic acid also forms which cannot be separated off or can be separated off only with great difficulty. Furthermore, the product from this synthesis is often obtained in discoloured form, meaning that the product is unsuitable for the desired cosmetic area of application.

There is therefore still a need for a process by which 2-phenylbenzimidazolesulphonic acid can be prepared in high purity and high yield and at the same time in a manner which is easy to carry out. The object was therefore to provide a novel process for the preparation of 2-phenylbenzimidazolesulphonic acid.

Surprisingly, it has now been found that isolated 3,4-diaminobenzenesulphonic acid can be reacted with benzaldehyde and sulphurous acid to give 2-phenylbenzimidazole-5-sulphonic acid, which is obtained here in excellent yield and high purity. Optionally after single redissolution from an aqueous medium, this product is so pure, in particular it is bright white, that it can be used for cosmetic purposes.

This could not have been predicted from the described prior art.

The invention therefore provides a process for the preparation of 2-phenylbenzimidazole-5-sulphonic acid, characterized in that 3,4-diaminobenzenesulphonic acid is reacted at a pH between 4 and 7 in aqueous solution with 0.9 to 1.5 mol of benzaldehyde per mole of 3,4-diaminobenzenesulphonic acid and with 1.0 to 3.0 mol of $SO_2$ per mole of 3,4-diaminobenzenesulphonic acid, or an agent which comprises 1.0 to 3.0 mol of $SO_2$ per mole of 3.4-diaminobenzenesulphonic acid, and the resulting product is optionally purified by adding an oxidizing agent.

The required 3,4-diaminobenzenesulphonic acid was hitherto not industrially available; a new method for the preparation of this compound by sulphonation of 1,2-diaminobenzene, however, permits the production of large amounts of this preproduct and thus the technical advance described here.

In the process according to the invention, in a preferred embodiment, initially enough base is added to an aqueous suspension of 3,4-diaminobenzenesulphonic acid so that any adhering sulphuric acid is neutralized like the sulphonic acid. Suitable bases are LiOH, NaOH, KOH, lithium, sodium or potassium carbonate or bicarbonate, MgO, $MgCO_3$, but also organic bases, such as trialkylamine or pyridine, can be used stoichiometrically or as an additive of a few percent and in a mixture with other bases.

NaOH and KOH are preferred bases.

Overall, the total amount of the base is governed by the amount of adhering and contained acid; a pH of between 7 and 4 should be established, preference being given to a range from 6 to 5.

The amount of water used is likewise not critical; it is chosen according to stirrability on the one hand and the highest possible concentration for achieving a high space-time yield on the other hand.

A characteristic amount of water is from 0.5 to 3 litres, preferably 1–1.5 litres, per mole of starting material.

Then, sulphurous acid is added as $SO_2$-containing agent, preferably in the form of its alkali metal salts, e.g. $NaHSO_3$, $Na_2S_2O_5$ or $Na_2SO_3$, although it is also possible for $SO_2$ to be metered in as such in gaseous form and be reacted with bases in situ.

The role of the sulphite is two-fold:

On the one hand, the benzaldehyde which serves as reaction component is converted into a water-soluble form with the intermediate formation of sulphite adducts, such that the reaction takes place in a homogeneous medium; on the other hand, sulphite serves as an oxidizing agent for primarily formed 2-phenylbenzimidazolinesulphonic acid, which then converts to the desired phenylbenzimidazolesulphonic acid.

The salts used are preferably $NaHSO_3$ or $Na_2S_2O_5$ or $Na_2SO_3$. Like any $SO_2$, they are likewise added in an amount which corresponds to an $SO_2$ amount of from 1 to 3 mol per mole of diaminobenzenesulphonic acid; particular preference is given to amounts in the range from 1.1 to 2.5 mol, particularly in the range from 1.2 to 2.2 mol/mol.

Finally, benzaldehyde is added in an approximately stoichiometric amount.

If the molar ratio is too low, the yield drops, and an excess of benzaldehyde may lead to contamination of the waste-water with this excess. In general, a molar ratio of from 0.85 to 1.5, preferably from 0.90 to 1.1, is used.

The process is carried out at temperatures between 25° C. and 130° C.; preferably in a range from 50 to 90° C., particularly preferably 60 to 80° C. The procedure is not particularly sensitive to variations in temperature; the temperature should not be too low since the reaction otherwise proceeds too slowly; at a processing temperature of significantly more than 100°, the use of a pressurized apparatus is necessary.

The reaction time required within the chosen range can be very readily ascertained by the person skilled in the art, e.g. using IR spectroscopy, HPLC, thin-layer chromatography or similar analytical methods. In the range from 60–80° C., the reaction can generally be carried out in the range from ½–2 hours.

Small amounts of solids and/or clouding can be removed using methods known to the person skilled in the art, e.g. by treatment with activated carbon, silica gel, cellulose powder, kaolin or similar auxiliaries which are separated off after the treatment, e.g. by filtration, centrifugation, membrane permeation and similar processes.

Preference is given to the use of adsorbents which also remove discolouring secondary components from the solution; various standard commercial types of activated carbon, such as norite, are particularly suitable.

The clear-filtered solution is then acidified with acid. Suitable for this purpose are sulphuric acid, as well as hydrochloric acid or acetic acid. The use of acetic acid has proven particularly successful.

The desired product precipitates out and can be converted into a particularly readily filterable form by suitable temperature control and/or the addition of crystal germs. Methods of this type are known to the person skilled in the art.

Finally, the product is isolated by filtration, centrifugation or similar methods, washed (in order to remove salts) and either dried or further processed in the moist state.

If the resulting purity, particularly the optical aspect, still does not satisfy the requirements, the product can be dissolved again in an alkali and optionally treated with small amounts of oxidizing agents. Examples of suitable oxidizing agents which can be used are: $KMnO_4$; $FeCl_3$; chlorine lye; hydrogen peroxide, also in the form of adducts with urea or sodium borate; $K_2S_2O_8$; activated oxygen.

Potassium permanganate is particularly preferred. It is characteristically used in an amount of from 0.5 to 3 g per mole, preferably in an amount of 1–2 g per mole.

Preferably, after the reaction has been carried out, the product is isolated and dissolved; the oxidizing agent is then added, the mixture is clarified again using one of the abovementioned adsorbents, and separated and then the after-purified product is precipitated out again by acidification.

If sufficiently pure 3,4-diaminobenzenesulphonic acid is used, however, it is in most cases possible to dispense with the addition of oxidizing agents.

If the abovementioned 1,2-diaminobenzenesulphonic acid is used, this procedure is adequate for obtaining a product which satisfies most requirements.

In contrast to this, a 1,2-diaminobenzenesulphonic acid solution which is obtained by hydrogenation of 2-nitroaniline-4-sulphonic acid over Raney nickel or Pd/C in aqueous solution and from which the sulphonic acid is not isolated gives a crude product of 2-phenylbenzimidazole-5-sulphonic acid which has to be reprecipitated at least three, in most cases four to five, times in order to satisfy the purity requirements imposed by the cosmetics industry, specifically with regard to the pure white aspect.

The invention therefore further provides for the use of the 2-phenylbenzimidazole-5-sulphonic acid prepared according to the invention in cosmetic preparations.

EXAMPLES

Example 1

1250 ml of water are initially introduced and 1.0 mol of 3,4-diaminobenzenesulphonic acid is introduced (e.g. about 50% strength, sulphuric acid-moist; prepared from 1,2-diaminobenzene and sulphuric acid).

Sufficient NaOH (45–50% strength) is added dropwise to form a clear solution, and the pH is adjusted to 5.5. 200 g of $Na_2S_2O_5$ are added, the mixture is heated to 60° C. and 116 g (1.08 mol) of benzaldehyde are gradually added dropwise. The mixture is heated to 80°, stirred for 1 hour, clarified with 8 g of activated carbon and, after filtering off the activated carbon has been filtered off, acidified with acid (e.g. with acetic acid) at 80° C.

The mixture is stirred until cold, filtered with suction and washed with water.

This gives 320 g of moist product and, from this, 245 g of dry product (yield: 89.3%).

This product is already sufficiently pure for most intended uses.

If a particularly pure and particularly white product is desired, then this product can be dissolved again in dilute NaOH (optionally without intermediate drying), heated with activated carbon with the addition of a few grams of potassium permanganate and clarified, and again be precipitated by acidification.

This then gives 240 g of dry product (yield: 98.0%).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of 2-phenylbenzimidazole-5-sulphonic acid, comprising reacting 3,4-diaminobenzenesulphonic acid at a pH between 4 and 7 in aqueous solution with 0.9 to 1.5 mol of benzaldehyde per mole of 3,4-diaminobenzenesulphonic acid and with 1.0 to 3.0 mol of $SO_2$ per mole of 3,4-diaminobenzenesulphonic acid, or an agent which comprises 1.0 to 3.0 mol of $SO_2$ per mole of 3.4-diaminobenzenesulphonic acid, wherein the agent is alkali metal salts selected from the group consisting of $Na_2HSO_3$, $Na_2S_2O_5$ and $Na_2SO_3$.

2. Process according to claim 1, characterized in that 3,4-diaminobenzenesulphonic acid obtained by sulphonation of 1,2-diaminobenzene is used.

3. Process according to claim 1, characterized in that the reaction is carried out at a pH in the range from 5 to 7.

4. Process according to claim 1, characterized in that the benzaldehyde is used in an amount of from 1.05 to 1.1 mol/mol.

5. Process according to claim 1, characterized in that the reaction is carried out at a temperature in the range from 25° to 130° C.

6. 2-phenylbenzimidazole-5-sulphonic acid obtained according to claim 1 which is lightened by means of treatment with an oxidizing agent.

* * * * *